United States Patent
Bar et al.

(10) Patent No.: US 10,806,527 B2
(45) Date of Patent: Oct. 20, 2020

(54) SEMI-RIGID BONE ATTACHMENT ROBOTIC SURGERY SYSTEM

(71) Applicant: Mazor Robotics Ltd., Caesarea (IL)

(72) Inventors: Yossi Bar, Tirat Carmel (IL); Eliyahu Zehavi, Haifa (IL); Yonatan Ushpizin, Kibbutz Glil-Yam (IL)

(73) Assignee: MAZOR ROBOTICS LTD., Caesarea (IL)

( * ) Notice: Subject to any disclaimer, the term of this patent is extended or adjusted under 35 U.S.C. 154(b) by 714 days.

(21) Appl. No.: 15/104,529

(22) PCT Filed: Dec. 15, 2014

(86) PCT No.: PCT/IL2014/051096
§ 371 (c)(1),
(2) Date: Jun. 15, 2016

(87) PCT Pub. No.: WO2015/087335
PCT Pub. Date: Jun. 18, 2015

(65) Prior Publication Data
US 2016/0310221 A1    Oct. 27, 2016

Related U.S. Application Data

(60) Provisional application No. 61/916,240, filed on Dec. 15, 2013.

(51) Int. Cl.
*A61B 34/30* (2016.01)
*A61B 34/20* (2016.01)
(Continued)

(52) U.S. Cl.
CPC .............. *A61B 34/30* (2016.02); *A61B 34/20* (2016.02); *A61B 90/06* (2016.02);
(Continued)

(58) Field of Classification Search
CPC .... A61B 2034/2051; A61B 2034/2055; A61B 2034/2059; A61B 2090/064;
(Continued)

(56) References Cited

U.S. PATENT DOCUMENTS 5,408,409 A    4/1995 Glassman
5,806,518 A    9/1998 Mittelstadt
(Continued)

FOREIGN PATENT DOCUMENTS

FR    2983059 A1    5/2013
WO    2013084221 A1    6/2013

OTHER PUBLICATIONS

Supplementary European Search Report dated May 12, 2017, for EP 14869513.3, corresponding to the present application.
(Continued)

*Primary Examiner* — Samuel S Hanna
(74) *Attorney, Agent, or Firm* — Sheridan Ross P.C.

(57) ABSTRACT

A bone connection system for attaching a surgical robot having its base mounted in the vicinity of a patient, to a bone of the patient. The system incorporates a switchable bone connection unit attached between the bone and a support element of the robot. This unit has a locked state in which the bone is attached essentially rigidly to the support element, and a released state in which the bone can move relative to the support element. The unit comprises a force sensor for determining the force exerted between the bone and the support element of the robot, and a position sensor for measuring the position of the bone relative to the support element of said robot. The unit switches from its locked state to its released state when the force exceeds a predetermined level, selected to ensure that the bone can move without detaching any bone connection elements.

16 Claims, 7 Drawing Sheets

(51) Int. Cl.
*A61B 90/00* (2016.01)
*A61B 17/00* (2006.01)
(52) U.S. Cl.
CPC ............... *A61B 2017/00477* (2013.01); *A61B 2034/2051* (2016.02); *A61B 2034/2055* (2016.02); *A61B 2034/2059* (2016.02); *A61B 2090/064* (2016.02)
(58) Field of Classification Search
CPC .......... A61B 2017/00477; A61B 34/30; A61B 17/1624; A61B 17/1707; A61B 17/3494
See application file for complete search history.

(56) References Cited

U.S. PATENT DOCUMENTS

| | | | |
|---|---|---|---|
| 8,571,638 | B2 | 10/2013 | Shoham |
| 2005/0154493 | A1 | 7/2005 | Wang |
| 2009/0245956 | A1* | 10/2009 | Apkarian ............ A61B 17/1626 408/1 R |
| 2011/0015649 | A1 | 1/2011 | Anvari |
| 2011/0245833 | A1* | 10/2011 | Anderson .......... A61B 17/1626 606/80 |
| 2013/0096573 | A1 | 4/2013 | Kang et al. |
| 2013/0218216 | A1 | 8/2013 | Mast |
| 2014/0316436 | A1* | 10/2014 | Bar ........................ A61B 90/50 606/130 |
| 2014/0350571 | A1 | 11/2014 | Maillet et al. |
| 2016/0120553 | A1* | 5/2016 | Xie ...................... A61B 17/162 606/80 |

OTHER PUBLICATIONS

PCT International Search Report and Written Opinion of the ISA, dated Apr. 12, 2015, in PCT/IL2014/051096.

* cited by examiner

Fig. 5B

SEMI-RIGID BONE ATTACHMENT ROBOTIC SURGERY SYSTEM

CROSS REFERENCE TO RELATED APPLICATIONS

This application is a national stage application under 35 U.S.C. § 371 of PCT Application No. PCT/IL2014/051096, having an international filing date of Dec. 15, 2014, which designated the U.S., and which claims the benefits of and priority under 35 U.S.C. § 119(e) to U.S. Provisional Application Serial No. 61/916,240, filed on Dec. 15, 2013, entitled "Semi-Rigid Bone Attachment Robotic Surgery System."

FIELD OF THE INVENTION

The present invention relates to the field of robotic surgery using a robot attached to a bone of the subject, especially where selectable rigidity is required of the attachment elements, in order to enable the patient to move during surgery, such as breathing, without losing the positional relationship between the surgical tool and the patient's body part on which the operation is being performed.

BACKGROUND OF THE INVENTION

In a bone-mounted robotic surgical system, such as is described in U.S. Pat. No. 8,571,638, for "Miniature Bone-Attached Surgical Robot" to M. Shoham, the complete robot moves with movement of the patient's bone, such that the surgical tool held in the robotic arm does not move relative to its operating position with movement of the patient, such as during the breathing cycle.

However, when a conventional surgical robot is used, which is mounted in a fixed position, such as on the patient bed, or on the floor, or the ceiling next to the patient bed, the breathing of the patient causes the body part to move relative to the robot, such that there is a conflict between the fixed position of the robot base with its surgical tool attached to the actuating arm extremity, and the moving body part on which the robot is operating. In order to ensure accurate surgical performance, it is necessary to take into account the body movement. Some such systems track motion of the patient's body by means of a navigation system, which follows the position of the body part and compensates for this motion by adjusting the pose of the robot accordingly. Other such systems, such as U.S. Pat. No. 5,806,518 to B. Mittelstadt for "Method and System for Positioning Surgical Robot", use a bone fixation element and a bone follower element which follows motion of the bone, and provides a feedback signal to the robot to correct therefor. Yet other systems, such as that described in PCT application No. PCT/IL2012/000387 for "Active Bed Mount for Surgical Robot" having a common inventor with the present application, provide a rigid connecting link between the robot arm and the patient's body part, in order to connect the spatial positions of the body part, and the robot operating arm. The rigid connection link incorporates a force sensor, and the force exerted on this connection link is measured for use in a feedback servo system to control the motion of the mechanical support element of the activated robot arm to allow it to move with motion of the patient's bone, thus maintaining the spatial position of the surgical tool relative to the patient's bone.

However, in bed or floor mounted systems in which no such active control is used, there exists the problem of how to accommodate for motion of the patient's body since the robot activated arm extremity has to be positively correlated to the position of the body part being operated on. The connection of the robot to the patient's bone will try to suppress motion of the patient's bone, which it may partially succeed in doing, especially if the chest of the patient is supported in such a manner that it can expand freely, since both the connection link itself and the robotic arm links have some element of flexibility. Ultimately however, since such patient movement as breathing motion cannot be completely suppressed, the connection link may become detached from the patient's bone, and the reference position of the robot relative to the patient's body part will be lost.

There therefore exists a need for providing a system for enabling spatial attachment of the robotic arm to the patient's body part being operated on, but without limiting the patient's ability to move his/her body within prescribed limits, and which therefore overcomes at least some of the disadvantages of prior art systems and methods.

The disclosures of each of the publications mentioned in this section and in other sections of the specification, are hereby incorporated by reference, each in its entirety.

SUMMARY

The present disclosure describes new exemplary systems for robotic surgery on a patient, including a connection link between the support member for the robotic arm and the patient's body part on which the operation is being performed. The body part used is generally a bone, as this provides firm clamping and a defined clamping position. Since most applications will be concerned with attachment to a patient's bone, bone attachment will be used throughout this disclosure as a selected example of the application of the system, though it is to be understood that the application is not intended to be limited to use for bone connection. For this reason, the operating mechanism installed on the connecting link is called hereinafter a "Bone Connection Unit" or BCU, though understood not to be limited thereto.

The robotic arm support element or support structure is interpreted in this disclosure to encompass any type of mechanical member, structure or even arms, situated between the true robot base and those parts of the robot mechanism which are activated such that their settings or motion define the robotic pose of the end actuator relative to the patient's body. In this respect, all parts of the robot, from its true base up to the point of attachment of the connecting link to the robot support element, can be considered to be part of the so-called "virtual base" of the robot, since all of those parts are fixed relative to the patient, any active links in that "base" section being locked for this purpose. On the other hand, all of those sections of the robot beyond the point of attachment of the connection link to the support element, which could include one or more activated robotic links, can be considered to be the active robot itself.

The connection link described herein differs from prior art connection links in that it incorporates two sensors, and the system includes their associated operating mechanisms and circuitry:

(i) A force sensor to determine the longitudinal force exerted on the connection link between the bone and the robotic arm support structure. The force sensor is adapted to release the connection link from the robotic arm support when that force exceeds a predetermined level. That level is selected to ensure on the one hand that it is sufficiently low so that the patient does not encounter undue discomfort or have his/her breathing compromised, and on the other hand, that it is sufficiently high so that the connection link does not completely detach itself from the body part to which it is connected, rather than actuating its release mechanism as intended. Although the usual meaning of the term "force sensor" is for a device for measuring force, it is to be noted that in this disclosure, the term "force sensor" is used to mean a device for sensing the force applied to enable performance of an action or actions in accordance with the force sensed, such as the locking or release of the connection link from the BCU body, and not necessarily for merely measuring the force.

(ii) A position sensor to track the position of the connection link relative to the robotic support structure, so that when the connection link is detached from the robotic support structure by actuation of the force sensor mechanism of paragraph (i) above, the exact position of the connection link is known at all stages of its motion. Then, when the movement of the patient's body subsides, the connection link can be reattached to the robotic support structure at exactly the same position as that to which it was attached before detachment, thereby maintaining the known spatial relationship between the surgical tool at the end of the robotic arm and the patient's body part. As an alternative, since the position of the connection link is known wherever it is in its range of motion, the connection link can be reattached at any predetermined position and appropriate correction made to the robot positioning data.

In addition, when the connection link is released and is moving freely relative to the activated robotic arm, its position should be continually relayed from the BCU controller to the robotic controller, in order to update the robot controller with the position of the patient's bone being operated on. Without that information, registration of the location of the robotically guided surgical tool with the patient's bone would be lost, rendering the robotically guided system as ineffective.

These sensors are most conveniently incorporated into a single unit, disposed on the connecting link between the clamp to the patient's body part (such as a bone) and the attachment point to the robot arm support element. Although the most convenient location for installing this unit is where the connecting link is attached to the robot support element, it is to be understood that it could also be installed at any other point along the connecting link, or even at the patient bone attachment clamp. Furthermore, the force sensor may alternatively be installed on the connection link, such as by attachment of one or more strain gauge force sensors thereto, and not within the single unit.

Use of the novel connecting link construction described in this disclosure has the effect of virtually relocating the base position of a bed-mounted or floor mounted robot to the patient's bone in the region where the operation is being performed. In this respect, the present system can convert any robot, even of size and weight that will not enable it to be supported on the bone, to a pseudo "bone mounted" robot, with all of the advantages which that configuration provides with respect to defining the robot position to the patient's body part. This system is therefore important in spinal surgery, where the patient's breathing motions need to be taken into account continuously in order to maintain the accuracy of the robotic registration. The system may thus be described as being a semi-rigid bone connection system, since the bone attachment property can be described as having rigid and non-rigid configurations, automatically switchable according to the force applied to the unit by any movement of the patient to which the system is attached.

In order to provide fast and simple operation, the BCU mechanism is generally electro-mechanical, conveniently incorporating mechanical spring sensors, solenoids and position sensors, whether magnetic or optical or otherwise.

There is thus provided in accordance with an exemplary implementation of the devices described in this disclosure, a bone connection system for attaching a surgical robot having its base mounted in the vicinity of a subject, to a bone of the subject, the system comprising a switchable bone connection unit attached between the bone and a support element of the surgical robot, the switchable bone connection unit having a locked state in which the bone is attached to the support element, and a released state in which the bone can move relative to the support element, the switchable bone connection unit comprising, (i) a force sensor for determining the force exerted between the bone and the support element of the robot, and (ii) a position sensor for measuring the position of the bone relative to the support element of the robot, wherein the switchable bone connection unit is adapted to switch from its locked state to its released state when the force exceeds a predetermined level.

In such a system, the switchable bone connection unit may be further adapted to switch from its released state to its locked state when the measured position shows that the bone has returned to a predetermined position relative to the support element of the robot. Furthermore, the bone connection unit may also be adapted to utilize the measured position of the bone relative to the bone connection unit such that the bone connection system instructs the robot to adjust the position of its activated arm extremity such that the position of the activating arm extremity relative to the bone is maintained during the released state of the bone connection unit. In either of the latter two cases, the predetermined position may be the position of the bone relative to the bone connection unit when the bone connection unit was in its initial locked state.

Furthermore, in any of the above-described systems, the bone connection system may also comprise a connection link which is attached either between the bone connection unit and the bone, or between the bone connection unit and the support element. In either such case, the system may further comprise a spring disposed such that motion of the connection link against the spring enables determination of when the force exerted between the bone and the support element exceeds the predetermined level. That spring may be either preloaded or unloaded.

Additionally, in any of the above described systems incorporating a connection link, the bone connection unit may comprise a solenoid actuated element having at least one protrusion which is adapted to mesh with at least one matching hollow in a body within which the connection link can move, such that meshing of the at least one protrusion with the at least one hollow switches the bone connection unit into its locked state. Alternatively, the connection link may comprise an asymmetric shaft disposed off-center in a cylindrical bore in the bone connection unit, such that rotation of the shaft either locks or releases motion of the connection link.

In general, in any of the above described bone connection systems, the force sensor may be located either within the bone connection unit or on the connection link. The robot itself may be bed-mounted or floor mounted or ceiling mounted. Additionally, the bone connection unit may be attached either to an element of the robot situated between its base and its activated arm extremity, or to the bone of the subject. Furthermore, the position sensor may be either an optical or magnetic linear encoder, or an opto-electronic switch.

According to yet further implementations, in the bone connection systems described in this disclosure, the bone connection unit may be attached to the robot at an intermediate joint of the robot, in which case those joints of the robot between its base and the intermediate joint should be locked such that the effective base of the robot is transferred to the location of the attachment of the bone connection unit to the robot.

Yet other implementations of those above described bone connection systems comprising a connection link may further comprise:
(i) a spring loaded plunger located in the housing of the bone connection unit, and
(ii) a groove located on the circumference of the connection link, wherein the locked state is then obtained when the spring loaded plunger is located within the groove, and the released state is obtained when the spring loaded plunger is located out of the groove, and wherein at least the force on the spring loaded plunger and the wall profile of the groove are selected such that the bone connection unit switches from its locked state to its released state when a predetermined force is applied on the connection link.

Yet other implementations described in this disclosure perform a method of attaching a surgical robot mounted in the vicinity of a subject to a bone of the subject, comprising:
(i) connecting the bone to a support element of the robot by means of a switchable bone connection unit having a locked state in which the bone is attached to the support element, and a released state in which the bone can move relative to the support element,
(ii) detecting the force exerted between the bone of the subject and the support element of the robot,
(iii) measuring the position of the bone relative to the support element of the robot, and
(iv) switching the bone connection unit from its locked state to its released state when the force exceeds a predetermined level.

Such a method may further comprising the step of switching the bone connection unit from its released state to its locked state when the measured position shows that the bone has returned to a predetermined position relative to the support element of the robot. Furthermore, the method may further comprise the step of utilizing the measured position of the bone relative to the bone connection unit to instruct the robot to adjust the position of its activated arm extremity such that the position of the activating arm extremity relative to the bone is maintained when the bone connection unit is in its released state. In either of the latter two cases, the predetermined position may be the position of the bone relative to the bone connection unit when the bone connection unit was in its initial locked state.

Furthermore, in any of the above-described methods, the bone connection system may also comprise a connection link attached either between the bone connection unit and the bone, or between the bone connection unit and the support element. In either such case, the force sensor may utilize the motion of the connection link against a spring to determine when the force exerted between the bone and the support element exceeds the predetermined level. The spring may be either preloaded or unloaded.

Additionally, in any of the above described methods involving a connection link, the bone connection unit may comprise a solenoid actuated element having at least one protrusion which is adapted to mesh with at least one matching hollow in a body within which the connection link can move, such that the bone connection unit is switched into its locked state by meshing of the at least one protrusion with the at least one hollow. Alternatively, in these methods involving use of a connection link, the connection link may comprise an asymmetric shaft disposed off-center in a cylindrical bore in the bone connection unit, such that motion of the connection link is locked or released by rotation of the shaft.

In any of the above described bone connection systems, the force sensor may be located either within the bone connection unit or on the connection link. The robot itself may be bed-mounted or floor mounted or ceiling mounted. Additionally, the bone connection unit may be attached either to an element of the robot situated between its base and its activated arm extremity, or to the bone of the subject. Furthermore, the position sensor may be either an optical or magnetic linear encoder, or an opto-electronic switch.

According to yet further implementations, in the methods described in this disclosure, the bone connection unit may be attached to the robot at an intermediate joint of the robot, in which case those joints of the robot between its base and the intermediate joint may be locked such that the effective base of the robot is transferred to the location of the attachment of the bone connection unit to the robot.

In yet other implementations of those above described methods involving use of a bone connection system incorporating a connection link, the bone connection unit may further comprise:
(i) a spring loaded plunger located in a bore in the housing of the bone connection unit, and
(ii) a groove located on the circumference of the connection link,
wherein the locked state is obtained when the spring loaded plunger is located within the groove, and the released state is obtained when the spring loaded plunger is located out of the groove, and wherein at least the force on the spring loaded plunger and the wall profile of the groove are selected such that the bone connection unit switches from its locked state to its released state when a predetermined force is applied on the connection link.

BRIEF DESCRIPTION OF THE DRAWINGS

The present invention will be understood and appreciated more fully from the following detailed description, taken in conjunction with the drawings in which.

DETAILED DESCRIPTION

Figure 1A:
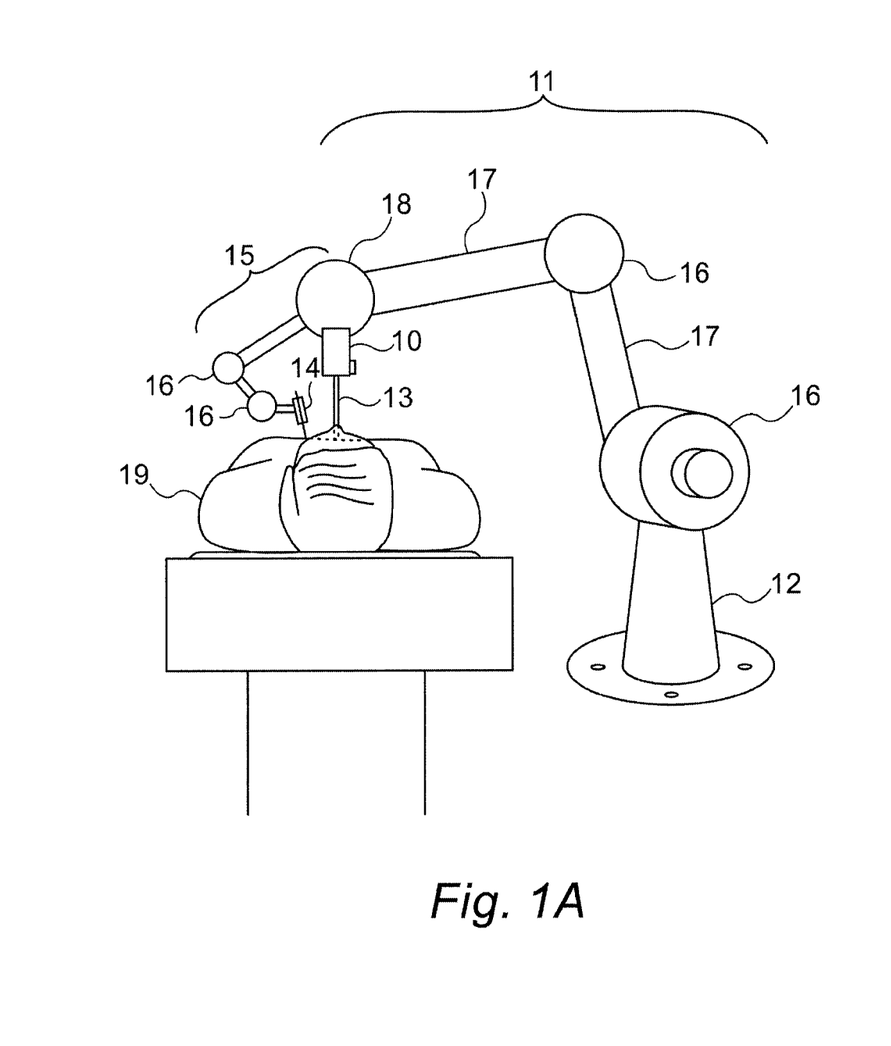
FIGS. 1A and 1B illustrate schematically isometric views of an exemplary Bone Connection Unit (BCU) installed on a floor mounted robot.
Figure 1B:
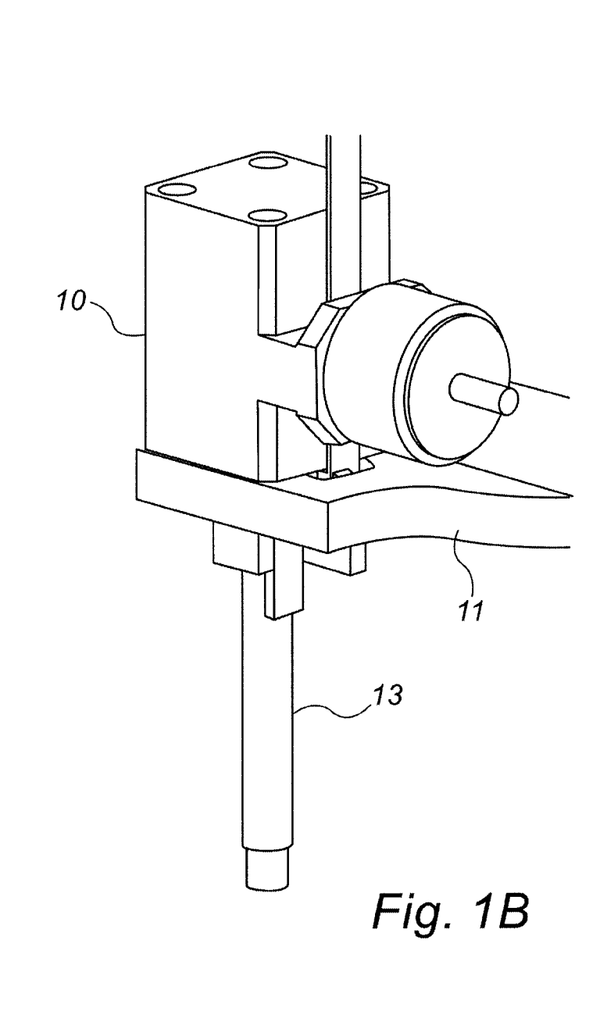

Reference is now made to FIGS. 1A and 1B, which illustrate respectively schematic isometric views of an exemplary Bone Connection Unit (BCU) 10 installed on a bed or floor mounted robot 12. FIG. 1A is an overall view of an exemplary floor-mounted robotic installation 12 next to a patient 19 on an operating table, though the robot could equally well be bed-mounted or ceiling-mounted. The robot includes a number of separate articulated controlled joints 16 between its various arms 17, which could provide motion both in the plane of the drawing and out of it, thereby providing multiple degrees of freedom. The BCU 10 is shown attached rigidly to one 18 of the joint housings of the robot, close to the patient 19, so that a connection link 13 can be attached between a bone of the patient and the BCU 10. Connection to the bone may be made by a bone clamp, or a K-wire, or any other suitable method. The section of the robot from its true base up to the BCU is termed the robotic support structure 11, or the robot base arm, since it acts as a rigid support body, even though it may incorporate a number of robotic joints 16, since those joints are locked into position once that part of the robot has been brought into the correct position to enable the connection link 13 to be aligned above the attachment point in the patient's body. Those sections of the robot beyond the connection link are termed the activated robotic arm 15, since that is the part of the robot which is either controlled to take up the correct pose to enable the surgeon to accurately perform the surgery on the patient 19, or is even controlled to move such that it performs the surgical actions required. The activated robotic arm 15 may have a number of controlled joints 16 to enable it to adopt its desired pose, and, as will be seen hereinbelow, to compensate for motion of the patient. At the end of the activated robotic arm 15, an exemplary surgical tool, such as a guide cannula 14, is shown. The connection link 13 itself may be a K-wire or any other suitable rigid element which can be attached to the patient's bone or other body part, either directly or through an additional connection element, such as a bone clamp.

In that respect therefore, all of the robot sections from its true base up to the point 18 at which the BCU 10 is attached, can be considered as being a virtual robotic base 11, supporting the activated robotic arm 15, so that the static base of the robot is effectively transferred to the BCU 10 close to the patient. Like the true base of the robot, the BCU "virtual base" 11 does not move during the surgical procedure.

FIG. 1B is a close up view of the BCU 10 itself, showing the connection link 13 protruding from its lower extremity, while its body is firmly mounted onto the robotic support structure 11, which is a firmly attached part of the virtual robot base.

Figure 2:
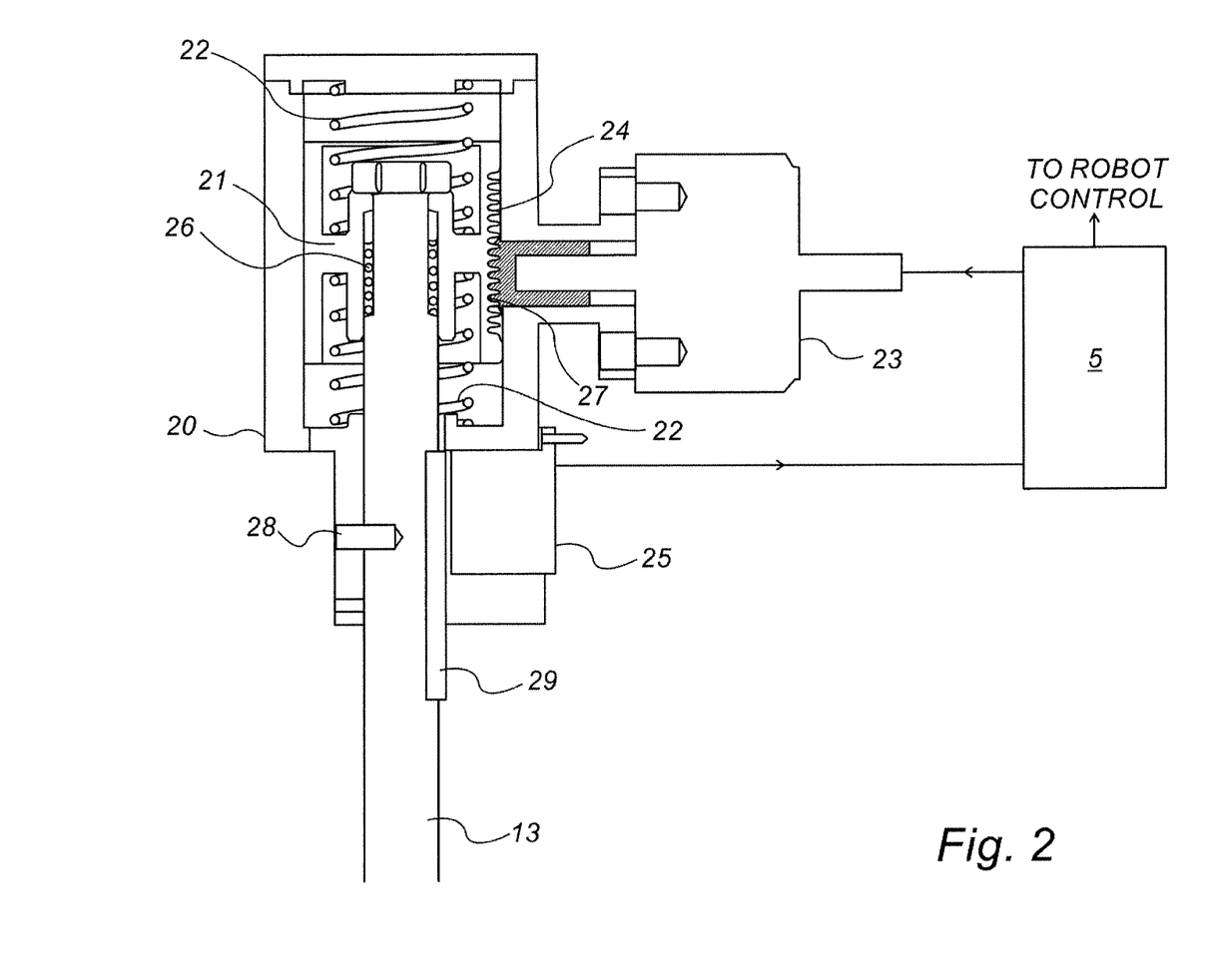
FIG. 2 is a schematic cut-away view of an exemplary BCU, to illustrate one method and structure by which the BCU can operate as a switched bone connection member, using a spring to measure the threshold at which it switches its clamping status.

Reference is now made to FIG. 2, which is a schematic cut-away view of an exemplary BCU, in order to illustrate one exemplary method and structure by which the BCU can operate. The operating mechanism of this BCU is contained within a housing 20, which is rigidly attached to the robotic support structure 11 of FIGS. 1A and 1B. The connection link 13, which should be attached to the patient's bone at its distal extremity, is mounted within a floating bushing 21 which fits within the inner bore of the housing 20, and can slide longitudinally therein to enable the connection link to move. Motion of the floating bushing within the BCU housing can be disabled by means of a locking arrangement controlled by a solenoid 23, which can prevent the floating bushing from moving longitudinally within the housing, and can do so by locking the floating bushing 21 at any position longitudinally within the housing 20. In the example BCU structure shown in FIG. 2, this locking arrangement may typically comprise a set of teeth or grooves 24 arranged along a length of the outer wall of the floating bushing, and one or more projections which can conveniently be in the form of opposing teeth 27, which are attached to the operating rod of the solenoid 23, such that the toothed projection(s) can be made to mesh with the teeth or grooves 24 of the floating bushing to lock it in place. The circumstances under which this locking is implemented are explained hereinbelow. When the locking arrangement is not engaged, and the floating bushing can move, its motion is constrained by means of two floating springs 22 each of which abuts against one end of the inner bore of the housing, such that motion of the floating bushing is damped.

The position of the connection link 13 relative to the BCU housing should be monitored by means of a position sensor, shown in the example BCU of FIG. 2 by means of an optical or magnetic linear encoder 25, 29. Typically, the motion of a magnetic or optical bar pattern encoder 29 attached to the connection link is detected and measured by the head of the position sensor 25, such that the longitudinal position of the connection link relative to the housing, and hence, its position and motion absolutely in patient space, is known.

Motion of the connection link 13 within the floating bushing is constrained by means of a force spring 26. The force spring 26 should be pre-loaded with the predetermined force exerted on the connection link by motion of the patient, at which it is determined that the connection link needs to be released from the robotic arm support. For operations on the spine of a patient, this force level is typically set at about 1 kg., or slightly less. This level can be adjusted by means of an adjustment screw (not shown). So long as the force exerted on the connection link does not exceed the preloading on the force spring, the connection link does not move within the bore of the floating bushing, and the force is contained within the force spring, counteracting the preload force. Consequently, no motion is detected by the position sensor 25. When the force exerted by the patient on the connection link does exceed the preloading force, the connection link 13 begins to move longitudinally into the inner bore of the floating bushing 21, and this initial movement is detected by the position sensor 25, whose signal is input to the BCU controller 5. Preloading the force spring thus has the advantage that an accurate registration of the robot to the bone is maintained right up until the motion commences. However, for less accurate applications, the force spring need not be preloaded, and the small motion of the connection link pushing against the force spring 26 is measured by the position sensor 25. As soon as the measured motion of the connection link indicates, by use of preliminary calibration, that the force exerted thereon exceeds the predetermined force level at which the connection link must be released, the BCU controller 5 outputs a signal, as in the previous embodiment.

According to either of the above spring configurations, this signal performs two actions:
(i) it records the position of the connection link 13, and
(ii) it activates the solenoid 23 to retract the protrusions 27 from the locking teeth 24, and to hold it in the retracted position, such that the entire floating bushing 21 can now move within the BCU housing.

Activation of the BCU release mechanism means that the connection link 13 and its floating bushing 21 are free to move within the fixed BCU housing 20 and hence relative to the fixed robotic support structure 11, to enable patient movement (such as breathing) to be accomplished, as intended. The two floating springs 22, on either end of the floating bushing 21, enable the floating bushing to rise and fall in a constrained manner with the breathing motion of the patient. The BCU controller 5 follows the position of the connection link 13 by means of the position sensor 25 output signal, and when the connection link 13 returns to its original equilibrium starting position, as recorded by the BCU controller 5, the controller issues a signal to the solenoid 23 to lock the protrusions 27 back into the locking teeth 24 of the floating bushing 21. The system is then locked with the connection link 13 rigidly held relative to the robotic support structure 11, ready to detect a further patient movement whose resulting force exceeds the predetermined threshold, at which point the connection link 13 is unlocked again.

However, during that part of the operation cycle of the BCU when the connection link 13 is free to move, the position of the body part or bone changes in relation to the position of the robotic support structure 11. Therefore, the position of the surgical tool at the end of the activated robotic arm 15, which defines the position at which the surgical process on the body part or bone is being performed, also changes, thereby invalidating all previously known spatial relationship between the surgical tool and the body part or bone on which it is operating. In order to avoid this problem, the BCU controller 5 is adapted to also continuously transmit a correction signal to the robotic controller (not shown), based on the position signal received from the position sensor 25, in order to adjust the position of the surgical tool to its correct intended position, thereby compensating for the motion of the patient.

An initial equilibrium rest position of the connection link is determined by releasing the locking teeth 24, so that the floating bushing can move freely with the patient's breathing, in order to determine the range of movement of the connection link 13, and then locking the teeth 24 at a predetermined position, generally closer to the exhaled condition of the patient. However, although the most convenient method of operation may be obtained by referring back to the original equilibrium starting position, there is no necessity that the BCU be locked only when that position is reached again, since there could be situations where, because of gross movement of the patient, rather than the simple and limited movement because of the breathing cycle, the connection link may not get back to its original equilibrium starting position, and locking should then take place at a different position.

A pin 28 running in a groove in the connection link 13 may be used to prevent the connection link from turning relative to the housing 20, in order to keep the position sensor 25 correctly aligned with its bar pattern encoder 29

Figure 3A:
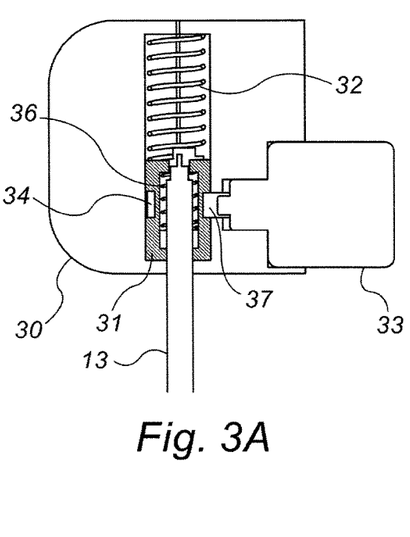
FIGS. 3A to 3D illustrate schematically different isometric and cut-away views of an alternative force sensing method to that of FIG. 2, in which the motion of the connection link due to the force exerted on it is detected by means of an opto-switch.
Figure 3B:
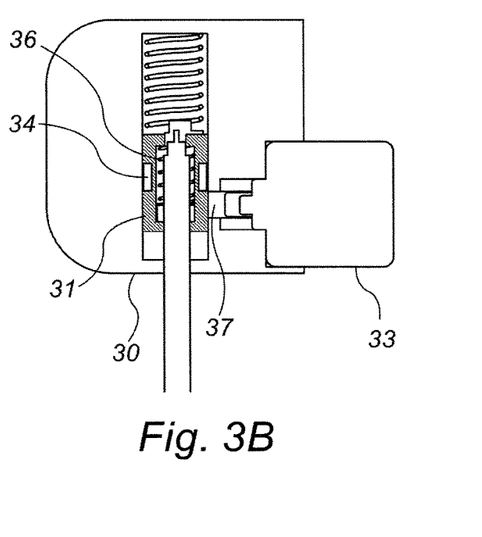
Figure 3C:
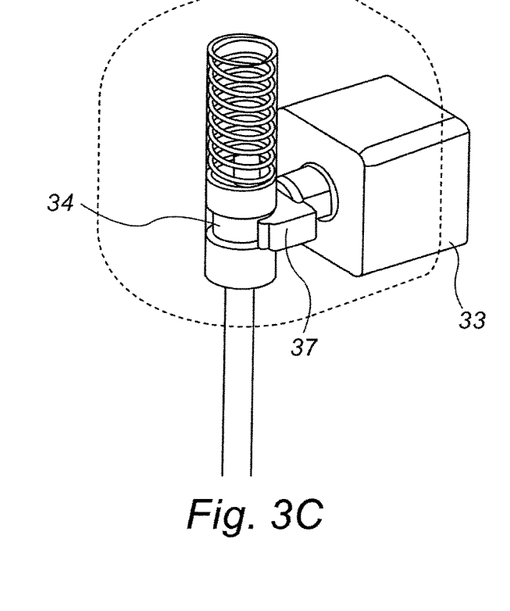
Figure 3D:
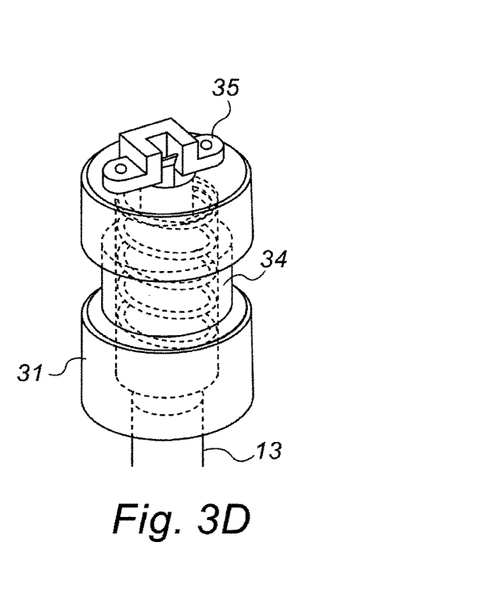

Reference is now made to FIGS. 3A to 3D, which illustrate schematically an alternative force sensing method, in which the motion of the connection link due to the force exerted on it is detected by means of an opto-switch. As in the implementation shown in FIG. 2, the connection link 13 is mounted within a floating bushing 31 which fits within the inner bore of the housing 30, and can slide longitudinally therein to enable the connection link to move. Motion of the floating bushing within the BCU housing can be disabled by means of a locking arrangement controlled by a solenoid 33. In the example BCU structure shown in FIGS. 3A-3D, this locking arrangement comprises a groove 34 cut in the outer wall of the floating bushing 31, and a two tongued open collar element 37, shown clearly in the isometric rendering of FIG. 3C, attached to the operating rod of the solenoid 33, so that when the collar element 37 is pushed into the groove 34, it locks the floating bushing 31 in place. Motion of the connection link 13 within the floating bushing 31 is constrained by means of a force spring 36, which compresses slightly as the force on the connecting link is increased. At the top of the floating bushing 31, as shown in FIG. 3D, an opto-switch 35 is positioned such that when the force on the connection link 13 increases above the predetermined level, the tip of the connection link 13 breaks the beam of the opto-switch 35, thereby providing a signal that the threshold force on the connection link has been reached. This signal is then processed by the BCU controller 5 to instruct the solenoid 33 to release the locking arrangement of the floating bushing 31. The connecting link is then free to move with the breathing of the patient, constrained only by the floating spring 32, which damps the motion and prevents the floating bushing from hitting the end plates of the housing with force. As with the implementation of FIG. 2, a position sensor is also required in order to define the reference position of the BCU with respect to the position of the robotically controlled or guided surgical tool.

Figure 4A:
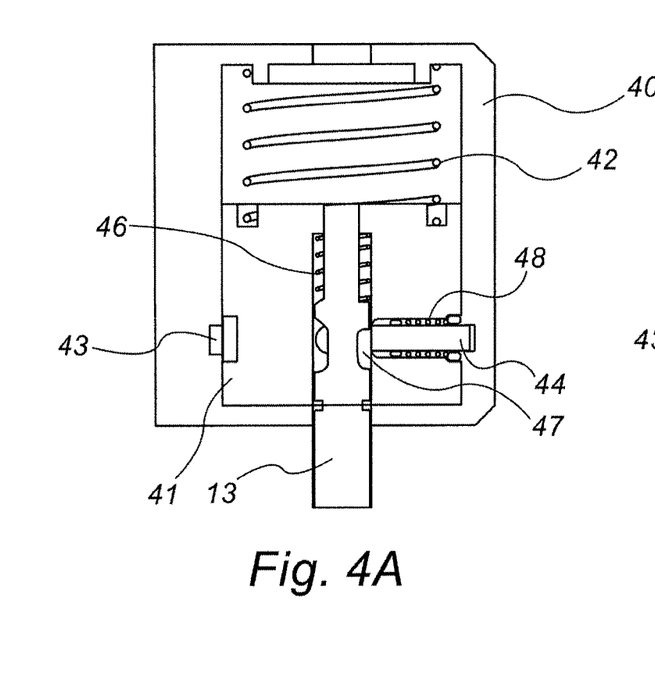
FIGS. 4A to 4C illustrates schematically yet another alternative implementation of the BCUs of the present disclosure, using a novel pin locking device for locking and releasing the floating bushing.
Figures 4B, 4C:
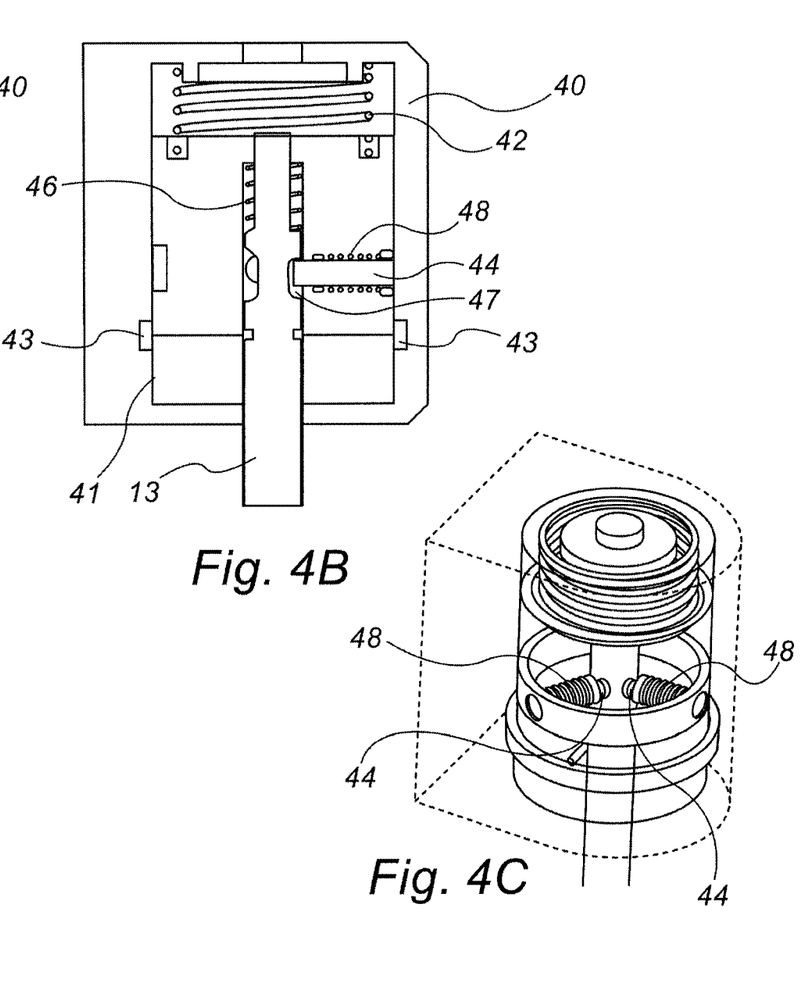

Reference is now made to FIGS. 4A to 4C, which illustrate schematically yet another alternative implementation of the BCUs of the present disclosure, using a novel pin 44 locking device for locking and releasing the floating bushing 41. Additionally, the pin 44 is used for determining when the force on the connecting link 13 is sufficient to cause the floating bushing 41 to be released so that it can move freely within the housing 40. As shown in FIG. 4A, in the locked position, the pin 44 rests on the outer surface of the connection link 13, such that the connection link 13 can move within the floating bushing 41, but the pin 44 protrudes radially out of the floating bushing 41 and into a circumferential groove 43 in the housing 40, such that the floating bushing is locked to the housing. The connecting link 13, as previously, operates against a force spring 46, which compresses as the force on the connecting link is increased. The connecting link 13 has a groove 47 in its outer surface, the groove being of dimensions such that the spring-loaded pin 44 located in a radial bore in the floating bushing 41, will slip into the groove 47 when the pin can move inwards towards the connection link, under the influence of its spring 48. The equilibrium longitudinal position of the connecting link within the floating bushing 41 is such that the pin 44 remains in its outer location resting on the outer surface of the connection link 13, until the force on the connection link reaches the predetermined threshold level, at which point connection link 13 has moved sufficiently inwards that the groove 47 is now in a position where the pin 44 can just slip into it under the influence of its spring 48. Once the pin 44 moves into the groove, as shown in FIG. 4B, it no longer protrudes into the circumferential groove 43 in the housing 40, such that the floating bushing 41 can now move freely within the housing 40, while at the same time, the pin 44 locks the connection link 13 to the floating bushing 41, such that they slide together within the bore of the housing 40. As previously a floating spring 42, controls excessively fast or extreme movement of the floating bushing 41. Although the above explanation has been presented using a single pin, it is to be understood that more than one pin 44, each with its bias spring 48, can also be used, as shown in the cut-away isometric drawing of this BCU in FIG. 4C.

Figure 5A:
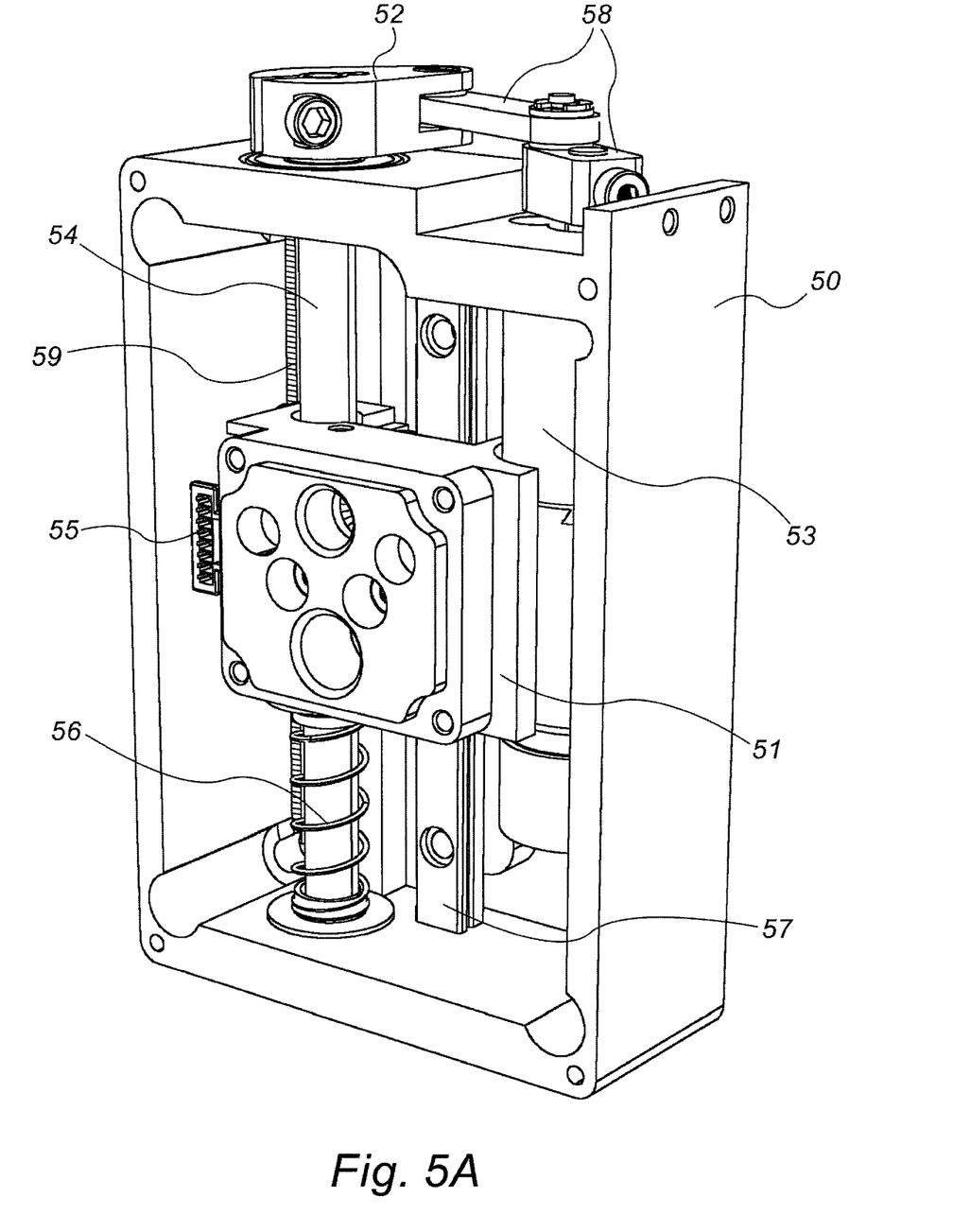
FIGS. 5A to 5C illustrate schematically yet another exemplary bone connection unit, also employing a spring-based force sensing method, but utilizing a cam-shaped shaft operating in a bore as the locking mechanism.
Figure 5B:
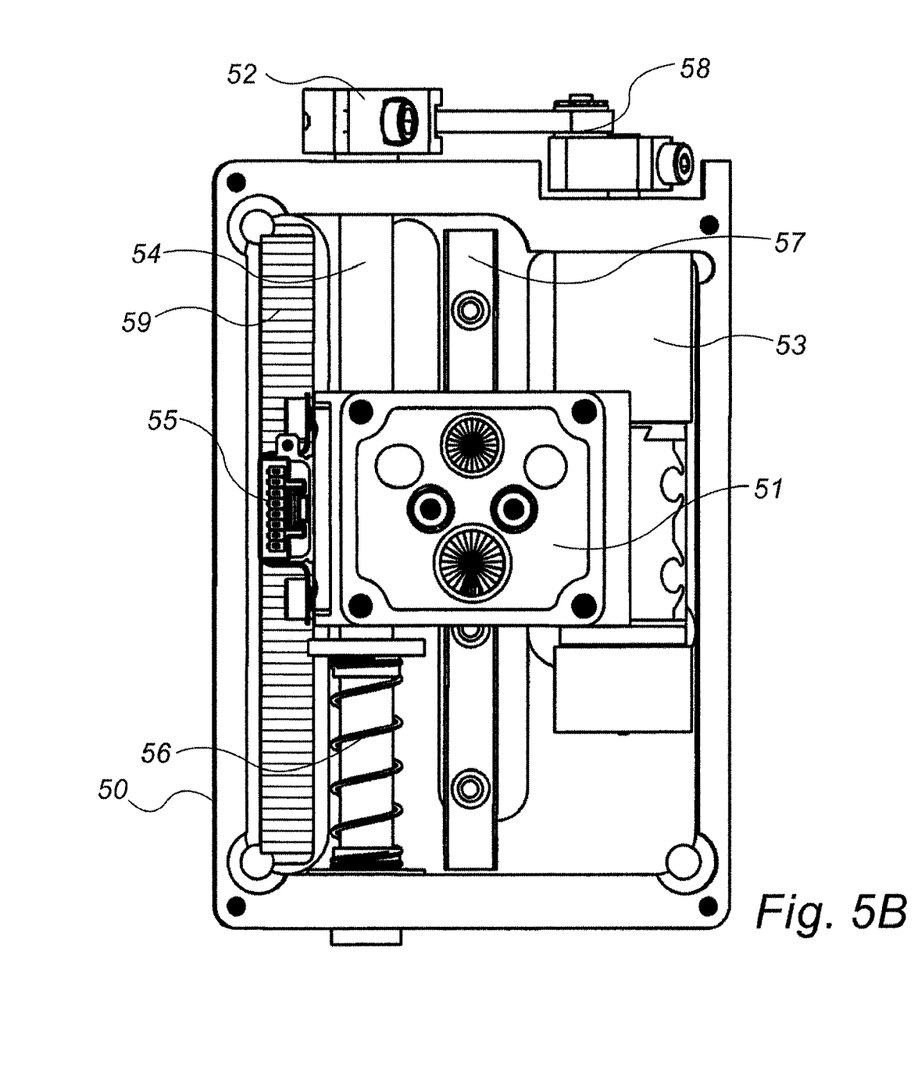
Figure 5C:
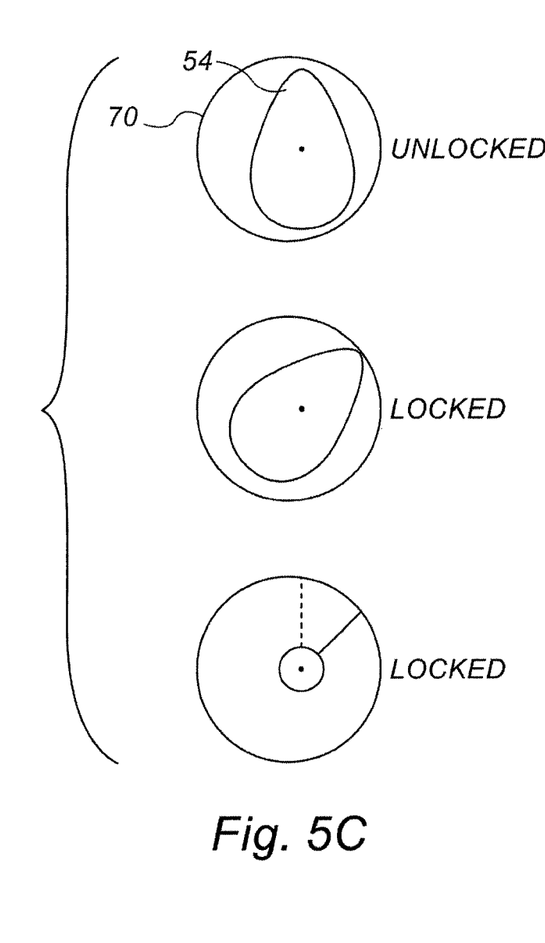

Reference is now made to FIGS. 5A to 5C, which illustrate schematically yet another exemplary bone connection unit, also employing a spring-based force sensing method. FIG. 5A is an isometric view of the BCU with its cover removed to show its working parts while FIG. 5B is a schematic drawing of the component parts, and FIG. 5C shows the operation of the locking mechanism. This implementation differs from those shown previously, in that the locking mechanism is based on a cam shaped shaft, which is rotated in a bore to lock the cam nose against the inside wall of the bore. In contrast to a toothed protrusion locking device, such as that shown in FIG. 2, where actuation of the locking device can cause unintended motion of the floating bushing by as much as half the pitch of the toothed rack into which the locking protrusion or protrusions are forced, use of such a rotating cam shaped shaft enables locking to be achieved without imparting any unintended longitudinal motion to the floating bushing.

As in the previous implementations, the housing 50 of the BCU is attached to the robotic support structure. A vertical slide rail 57 is fixed inside the housing 50, and the floating assembly 51 can slide freely on this rail unless locked by the locking mechanism. The K-wire or other connection link to the bone of the patient, (not shown in FIGS. 5A-5C) is attached to the floating assembly 51, such that as the patient moves, the floating assembly 51, when in its unlocked status, can move freely along its rail 57 in sympathy with the movement of the bone of the patient. The position of the floating assembly 51 is measured, as previously, by a position sensor, typically comprising a magnetic or optical bar pattern rule encoder 59, attached to the housing 50, and a position reading head 55 attached to the floating assembly 51.

Locking of the floating assembly is performed by means of the cam shaped shaft 54, running the length of the housing 50 through the bore in the floating assembly 51, the bore most conveniently being cylindrical. The bore is larger in diameter than the maximum dimension of the cam profile, namely from the cam nose to the opposite point on the base circle, such that the floating housing 51 can move freely along the cam shaped shaft 54. As shown in FIG. 5C, the center of rotation of the cam profile 54 is offset from the central axis of the cylindrical bore 70, such that when the cam shaped shaft is rotated, at some point of its rotation, the cam nose becomes wedged against the inside wall of the cylindrical bore 70, thereby locking the floating assembly 51 from further sliding along the cam shaped shaft 54. FIG. 5C shows the locked and unlocked positions of the rotating cam shaped shaft 54 in a cylindrical bore 70. In the cross sectional drawings of FIG. 5C, the center of rotation of the cam shaped shaft is shown to be slightly to the right of the center of the bore. Although a cam shaped profile is shown in the top two drawings of FIG. 5C, it is to be understood that the shaft could also have any other shape which includes an element which would wedge against the inner wall of the bore when rotated, such as a single protrusion ridge on a cylindrical shaft, as shown in the bottom drawing of FIG. 5C. Any such shaped shaft or rod is generically termed a "cam-shaped shaft" in this disclosure. Alternatively, an offset cylindrical shaft rotating in an oval or elliptical shaped bore could also be used, though production of a non-circular cross section bore may be less advantageous to manufacture. Rotation of the cam shaped shaft 54 can be achieved by means of a motor 53 operating an articulated link 58 connected to a rotary head 52 attached to one end of the cam shaped shaft 54.

Although a cylindrical bore may be the most convenient shaped bore to manufacture, it is to be understood that any other shaped bore which can be locked to a rotating camshaft can also be used. In an alternative design the bore in the sliding assembly 51 and cam shaped shaft 54 may have similar non circular cam shapes where the bore of the sliding assembly 51 is slightly larger in dimensions. As long as the cam shaft 54, and the sliding assembly bore are aligned conformally, the sliding assembly 51, can move freely along the cam shaped shaft 54. Once the cam shaft 54 is rotated, it presses against the bore in the sliding assembly and prevents its free motion. This particular implementation may even be advantageous over the use of a cylindrical bore, since the cylindrical bore may suffer from a lateral moment when the cam locks it.

The BCU operates as follows. The cam shaped shaft 54 is mounted in its end bushings or bearings in the BCU housing 50 in such a manner that it can undergo limited axial movement. End stops, such as circlips, may be used to limit the axial movement range of the cam shaped shaft, so that it does not slip out of its bore in the floating assembly. In normal use, when the floating assembly 51 is locked and the patient's bone makes a movement upwards (in the drawing frame of reference) towards the robotic arm, the connection link from the bone, not shown but attached to the floating assembly 51, attempts to move upwards, and the force exerted on the floating assembly 51 is transferred to the cam shaped shaft 54 to which it is locked. A preloaded force spring 56 is threaded on the cam shaped shaft 54, and the force exerted on the cam shaped shaft 54 attempts to move it axially in its end bearings against the preloaded force spring 56. When the force transmitted by the connection link exceeds the preloaded force on the spring 56, the cam shaped shaft begins to move axially, together with the floating assembly 51 locked to it, and this movement is detected by the position sensor 55, 59. As soon as the movement exceeds a predetermined level, an output signal is generated from the position sensor control unit which rotates the motor 53, which in turn rotates the cam shaped shaft 54 such that it becomes released from its locked status with the floating assembly 51, and enables the floating assembly with the attached connection link to move freely with motion of the patient's bone. As previously, the position of the floating assembly is registered at the moment that the locking mechanism is released, so that it can be re-locked at the same or a known position. The position of the floating assembly is monitored continuously, in order to provide the correction required to the position of the robotic arm, as the patient's bone moves. As an alternative to the implementation shown in FIGS. 5A and 5B, the spring 56 could be located above the floating assembly, in which case it does not require any preloading, and its compression causes the slight end movement of the cam shaped shaft 54, which generates the signal to unlock the cam shaped shaft 54 from the floating assembly 51.

Figure 6A:
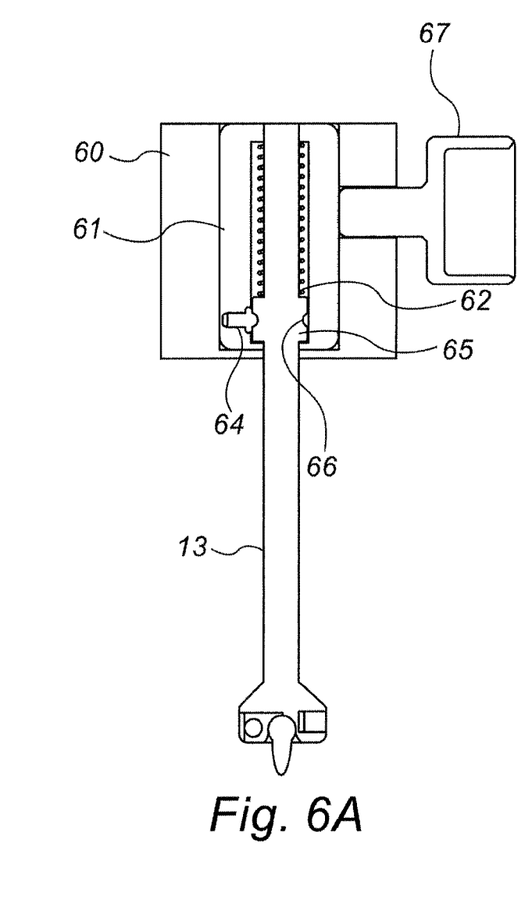
FIGS. 6A to 6C illustrate schematically yet another force sensing mechanism, which, unlike the BCU's shown in FIGS. 2 to 5C, is dependent on a plunger and indent ring groove mechanism for the force sensing rather than on a compressed spring.
Figure 6B:
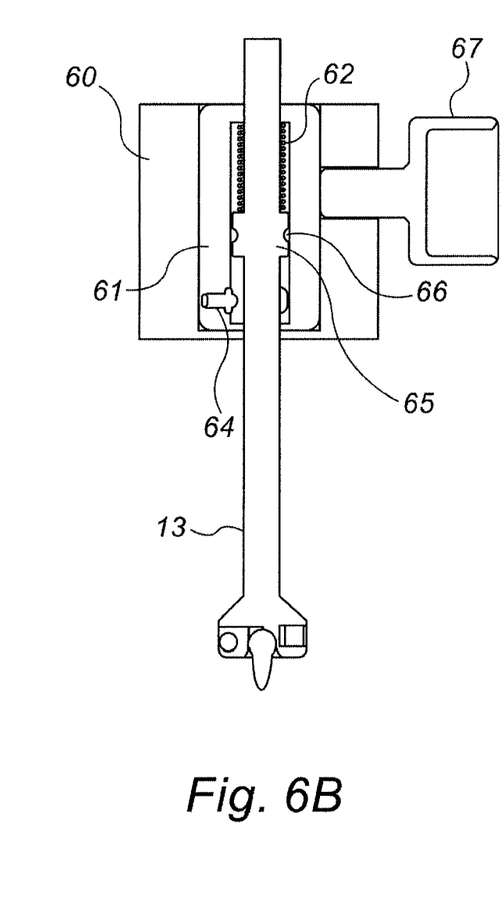
Figure 6C:
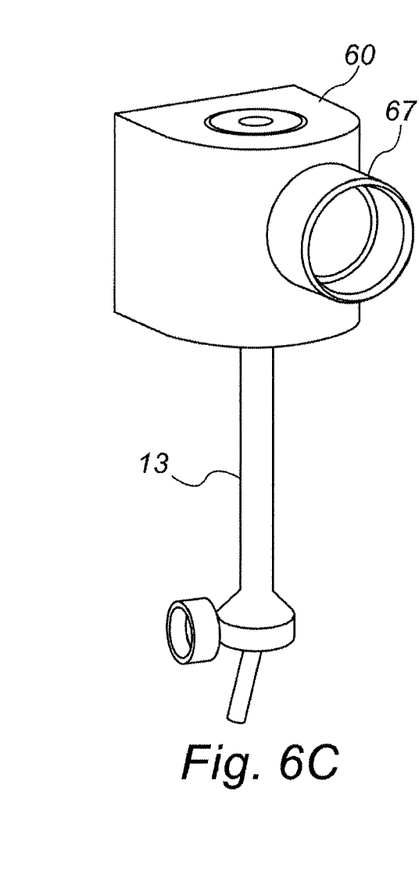

Reference is now made to FIGS. 6A to 6C, which illustrate schematically yet another force sensing mechanism, which, unlike the BCU's shown in FIGS. 2 to 5D, is dependent on a plunger 64 and ring groove 66 for the force sensing rather than on a compressed spring. FIGS. 6A and 6B show this implementation as sectional drawings of the device in its locked and unlocked statuses respectively, while FIG. 6C is an isometric external representation of this BCU implementation. In this implementation, the connection link 13 slides within an inner housing 61, whose position within the outer housing 60 can be adjusted by means of the adjustment handle 67. The motion of the connection link is damped by the floating spring 62, to prevent any extreme motion. The connection link has an enlarged diameter collar section 65 with an indent groove 66 formed within it. A spring-loaded plunger 64 is mounted in the inner housing 61, and in the BCU equilibrium position, the inner housing is adjusted such that the groove 66 on the connection link 13 falls exactly in line with the plunger 64, thus locking the connection link 13 to the inner housing 61 and outer housing 60. The shape of the plunger 64 and groove 66, and the preloaded spring force on the plunger are predetermined such that when the force on the connection link 13 exceeds the threshold level, the wall of the groove 66 manages to push the plunger 64 back out of the groove 66, and to allow the connection link 13 to escape from the restraining effect of the plunger. In that situation, the connection link becomes unlocked and can move freely with motion of the patient, until it returns to a position such that the indent groove 66 again receives the plunger 64, locking the connection link 13 again. As in previous implementations, a separate position sensor is required in order to reinstruct the robot control to take account of the movement of the connection link and the patient.

Considering an alternative form of operation of the BCU, it is observed that in the exemplary device shown in FIGS. 6A to 6C, and also that of FIG. 4, the locked position of the BCU is defined mechanically by the meshing of a protrusion in the BCU housing with a corresponding hollow or groove having a fixed position on the connection link. If the operation of the BCU is intended to allow the robot to operate on the patient only when the BCU is locked and the patient's bone is in the rest equilibrium position, then there is no need for a position sensor of the type described hereinabove, which measures the actual position of the connection link at all times. Instead, according to this simplified operational procedure, the position of the plunger in the opposing groove defines the position of the connection link relative to the robotic arm, and in that respect is a "position sensor", meaning that it senses when the locked status is operative or when the released status is operative, rather than that it measures that position absolutely.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

We claim:

1. A bone connection system for use with a robotic arm, comprising:
    a rigid connecting link having a length extending from a first end to a second end opposite the first end, the first end rigidly attachable to a bone to prevent movement of the connecting link relative to the bone along a direction parallel to the length;
    a support element configured to remain stationary notwithstanding movement of the bone while the first end is rigidly attached to the bone;
    a bone connection unit fixedly secured to the support element and connected to the connecting link, the bone connection unit comprising a position sensor configured to measure a position of the connecting link relative to the support element; and
    a force sensor configured to determine a force transmitted through the connecting link to the bone connection unit;
    wherein, when the force exceeds a predetermined level, the bone connection unit is configured to automatically, without manual intervention, switch from a locked state in which a position of the connecting link is substantially fixed relative to the bone connection unit, to a released state in which the connecting link is movable along at least a longitudinal axis thereof relative to the bone connection unit; and
    wherein the connecting link remains rigidly attached to the bone and in contact with the bone connection unit in the locked state and the released state.

2. The bone connection system of claim 1, wherein the bone connection unit is further adapted to switch from the released state to the locked state when the measured position shows that the connecting link has returned to a predetermined position relative to the support element.

3. The bone connection system of claim 2, wherein the predetermined position is a position of the connecting link relative to the bone connection unit when the bone connection unit is in the locked state.

4. The bone connection system of claim 1, wherein the bone connection unit is adapted to instruct a robotic activated arm, based on the measured position, to move so as to maintain a position of an extremity of the robotic activated arm relative to the bone while the bone connection unit is in the released state.

5. The bone connection system of claim 1, wherein the force sensor comprises a spring disposed to yield a predetermined amount when the force transmitted through the connecting link to the bone connection unit exceeds the predetermined level.

6. The bone connection system of claim 5, wherein the spring is either preloaded or unloaded.

7. The bone connection system of claim 1, wherein the bone connection unit comprises:
    a body within which the connecting link can move, the body comprising at least one hollow; and
    a solenoid-actuated element having at least one protrusion adapted to mesh with the at least one hollow,
    wherein meshing of the at least one protrusion with the at least one hollow switches the bone connection unit into the locked state.

8. The bone connection system of claim 1, wherein the connecting link comprises an asymmetric shaft disposed off-center in a cylindrical bore of the bone connection unit, such that rotation of the shaft either locks or releases motion of the connecting link.

9. The bone connection system of claim 1, wherein the force sensor is located either within the bone connection unit or on the connecting link.

10. The bone connection system of claim 1, wherein the support element is bed-mounted or floor-mounted or ceiling-mounted.

11. The bone connection system of claim 1, wherein the bone connection unit is attachable to the bone via the connecting link.

12. The bone connection system of claim 1, wherein the position sensor is an optical linear encoder, a magnetic linear encoder, or an opto-electronic switch.

13. The bone connection system of claim 1, further comprising:
    a spring loaded plunger located in a housing of the bone connection unit, and
    a groove located on a circumference of the connecting link,
    wherein when the spring loaded plunger is located at least partially within the groove, the bone connection unit is in the locked state, and when the spring loaded plunger is located out of the groove, the bone connection unit is in the released state.

14. The bone connection system of claim 13, wherein a wall profile of the groove is selected such that the bone connection unit automatically switches from the locked state to the released state when a predetermined force is applied to the connecting link.

15. The bone connection system of claim 1, wherein when the bone connection unit is in the locked state the connecting link has a first range of motion relative to the support element, and when the bone connection unit is in the released state the connecting link has a second range of motion relative to the support element, the second range of motion being substantially greater than the first range of motion.

16. A bone connection system for use with a robotic arm, comprising:
   a rigid connecting link having a length extending from a first end to a second end opposite the first end;
   a bone connection unit connected to the connecting link, the bone connection unit comprising a position sensor configured to measure a position of the connecting link relative to the bone connection unit; and
   a force sensor configured to determine a force transmitted through the connecting link to the bone connection unit;
   wherein, when the force exceeds a predetermined level, the bone connection unit is configured to automatically, without manual intervention, switch from a locked state in which a position of the connecting link is substantially fixed relative to the bone connection unit, to a released state in which the connecting link is movable along at least a longitudinal axis thereof relative to the bone connection unit; and
   wherein the first end of the connecting link is rigidly attachable to a bone, to prevent movement of the connecting link, relative to the bone along a direction parallel to the length in both the released state and the locked state; and
   wherein the connecting link remains in contact with the bone connection unit in both the released state and the locked state.

* * * * *